(12) United States Patent
Liu et al.

(10) Patent No.: US 8,487,125 B2
(45) Date of Patent: Jul. 16, 2013

(54) METHOD FOR PRODUCING CAFFEIC ACID PHENYL ESTER AND ITS ANALOGUES

(75) Inventors: Junyi Liu, Beijing (CN); Yansheng Du, Westfield, IN (US)

(73) Assignee: Chemigen, Indianapolis, IN (US)

( * ) Notice: Subject to any disclaimer, the term of this patent is extended or adjusted under 35 U.S.C. 154(b) by 52 days.

(21) Appl. No.: 12/543,691

(22) Filed: Aug. 19, 2009

(65) Prior Publication Data

US 2011/0046410 A1  Feb. 24, 2011

(30) Foreign Application Priority Data

Aug. 19, 2009 (CN) .......................... 2009 1 0166464

(51) Int. Cl.
*C07C 69/76* (2006.01)
(52) U.S. Cl.
USPC .......................................................... 560/61
(58) Field of Classification Search
None
See application file for complete search history.

(56) References Cited

U.S. PATENT DOCUMENTS

| | | | | |
|---|---|---|---|---|
| 4,699,925 A | * | 10/1987 | Uchida et al. | 514/559 |
| 5,008,441 A | | 4/1991 | Nakanishi et al. | |
| 5,696,223 A | * | 12/1997 | Karcher et al. | 528/422 |
| 6,313,165 B1 | | 11/2001 | Grunberger et al. | |
| 7,368,593 B1 | | 5/2008 | Prasad et al. | |

FOREIGN PATENT DOCUMENTS

EP  1 211 237  6/2002

OTHER PUBLICATIONS

Lee et al., "Preferential Cytotoxicity of Caffeic Acid Phenethyl Ester Analogues on Oral Cancer Cells," Cancer Letters 153:51-56 (2000).
Son et al., "Caffeic Acid Phenethyl Ester (CAPE): Synthesis and X-Ray Crystallographic Analysis," Chem. Pharm. Bull. 49(2):236-238 (2001).

* cited by examiner

*Primary Examiner* — Johann R Richter
*Assistant Examiner* — Jennifer C Sawyer
(74) *Attorney, Agent, or Firm* — Occhiuti Rohlicek & Tsao LLP

(57) ABSTRACT

A method for producing caffeic acid phenyl ester and its analogues, which includes the steps of: (i) reacting, in a solvent, a salt of a compound of formula (II)

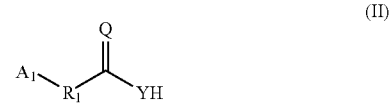

(II)

with an organic halide having the formula $X-R_2-A_2$ in the presence of an iodide catalyst having the formula M-I to produce caffeic acid phenyl ester or its analogue, wherein A1, R1, Q, Y, X, R2, and M are defined herein; and (ii) isolating the caffeic acid phenyl ester or its analogue from the solvent.

31 Claims, No Drawings

METHOD FOR PRODUCING CAFFEIC ACID PHENYL ESTER AND ITS ANALOGUES

CROSS-REFERENCE TO RELATED APPLICATIONS

This application claims priority to Chinese Patent Application No. 200910166464.9, entitled "Method for Producing Caffeic Acid Phenyl Ester and Its Analogues," filed Aug. 19, 2009, the content of which is hereby incorporated by reference in its entirety.

BACKGROUND

Caffeic acid phenethyl ester (CAPE), a plant-derived phenolic compound, is known to possess various pharmaceutical properties.

Several synthetic processes have been developed to produce CAPE and its analogues. Yet, there is a need for a higher-yield and higher-purity production method.

SUMMARY

The invention is based on an unexpected discovery that CAPE and its analogues, i.e., compounds of formula (I), can be produced in high yield and in high purity via a method which uses an alkali metal iodide catalyst.

More specifically, this invention relates to a method of preparing a compound of formula (I):

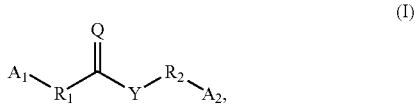

in which $R_1$ and $R_2$, independently, is $C_{1-8}$ alkylene, $C_{2-8}$ alkenylene, or deleted; each of $A_1$ and $A_2$, independently, is aryl or heteroaryl, optionally substituted with halogen, —CN, —$NO_2$, —OH, —SH, —$OR_3$, —$SR_3$, —$R_3$, —$R_3OR_4$, —C(O)$R_3$, —S(O)$R_3$, —S(O)$OR_3$, —$NR_4R_5$, —C(O)$NR_4R_5$, —OC(O)$R_4$, —$NR_4$C(O)$R_5$; and each of Q and Y, independently, is O, S, or $NR_6$; $R_3$ being $C_{1-4}$ alkyl and each of $R_4$, $R_5$, and $R_6$, independently, being H or $C_{1-4}$ alkyl.

The method includes two steps; namely, (i) reacting, in a solvent, a salt of a compound of formula (II):

with an organic halide having the formula X—$R_2$-$A_2$, wherein X is a halogen (e.g., Br, Cl, etc.), in the presence of an iodide catalyst having the formula M-I, wherein M is an alkali metal (e.g., Li, Na, etc.), to produce the compound of formula (I); and (ii) isolating the compound of formula (I) from the solvent.

Referring back to formula (I), exemplary compounds of this formula include those having: each of Q and Y, independently, being O; or $R_1$ being $C_{2-8}$ alkenylene (e.g., —CH=CH—) and $R_2$ being $C_{1-8}$ alkylene (e.g., —$CH_2$—$CH_2$—); or each of $A_1$ and $A_2$, independently, being aryl optionally substituted with —CN, —$NO_2$, —OH, —SH, —$OR_3$, —$SR_3$, —$R_3$, —$R_3OR_4$, or —$NR_4R_5$. An example of $A_1$ is 3, 4-dihydroxyphenyl and example of $A_2$ is phenyl.

The method for producing compounds of formula (I) can include, before the reacting step, contacting in a solvent the compound of formula (II) with a base to form the salt of the compound of formula (II).

The term "alkyl" refers to a straight or branched monovalent hydrocarbon (e.g., $C_1$-$C_4$). Examples of alkyl include, but are not limited to, methyl, ethyl, n-propyl, i-propyl, n-butyl, i-butyl, and t-butyl. The term "alkylene" refers to a straight or branched divalent hydrocarbon (e.g., —$CH_2$—$CH_2$—$CH_2$—). Examples of alkylene include, but are not limited to, methylene (—$CH_2$—) and ethylene (—$CH_2$—$CH_2$—). The term "alkenylene" refers to a straight or branched hydrocarbon, containing 2-8 carbon atoms and one or more double bonds (e.g., —CH=CH— or —CH=CH—CH=CH—). Examples of alkenylene include, but are not limited to ethene, propene, and butene.

The term "aryl" refers to a monovalent 6-carbon monocyclic, 10-carbon bicyclic, 14-carbon tricyclic aromatic ring system. Examples of aryl groups include, but are not limited to, phenyl, naphthyl, and anthracenyl. The term "heteroaryl" refers to a monvalent aromatic 5-8 membered monocyclic, 8-12 membered bicyclic, or 11-14 membered tricyclic ring system having one or more heteroatoms (such as O, N, S, or Se). Examples of heteroaryl groups include pyridyl, furyl, imidazolyl, benzimidazolyl, pyrimidinyl, thienyl, quinolinyl, indolyl, and thiazolyl.

Alkylene, alkenylene, aryl, and heteroaryl mentioned above include both substituted and unsubstituted moieties. Possible substituents on alkylene or alkenylene include, but are not limited to $C_2$-$C_{10}$ alkynyl, $C_3$-$C_{20}$ cycloalkyl, $C_1$-$C_{20}$ heterocycloalkyl, $C_1$-$C_{10}$ alkoxy, aryl, aryloxy, heteroaryl, heteroaryloxy, amino, $C_1$-$C_{10}$ alkylamino, arylamino, hydroxy, halo, oxo (O=), thioxo (S=), thio (—S—), silyl (—Si—), $C_1$-$C_{10}$ alkylthio, arylthio, $C_1$-$C_{10}$ alkylsulfonyl, arylsulfonyl, acylamino, aminoacyl, aminothioacyl, amidino, mercapto, amido, thioureido, thiocyanato, sulfonamido, guanidine, ureido, cyano, nitro, acyl, thioacyl, acyloxy, carbamido, carbamyl, carboxyl, and carboxylic ester. On the other hand, possible substituents on aryl and heteroaryl include all of the above-recited substituents in addition to $C_1$-$C_{10}$ alkyl. Aryl and heteroaryl can also be fused with each other.

The details of one or more embodiments of the invention are set forth in the description below. Other features, objects, and advantages of the invention will be apparent from the description and the claims.

DETAILED DESCRIPTION

The invention relates to method for producing a compound of formula (I) using an alkali metal iodide catalyst.

To practice the method of this invention, a salt of a compound of formula (II) is mixed with an organic halide described above (e.g., phenethyl bromide), in the presence of an alkali metal iodide catalyst (e.g., NaI), in a suitable solvent (e.g., dimethyl sulfoxide) to produce a compound of formula (I) (e.g., caffeic acid phenethyl ester). Examples of a suitable solvent include, but are not limited to, acetonitrile, acetone, hexamethyl phosphoramide, polyethylene glycol, water, dimethyl sulfoxide, acetone, dimethylformamide, or a mixture thereof. Preferably, the solvent is non-genotoxic.

In this method, the molar ratio of the salt of the compound of formula (II) to the organic halide can be within the range of about 1:1 to about 3:1 (e.g., 1.5:1).

Particular alkali metal iodide catalysts that are useful in this method include NaI, KI, LiI, or a combination thereof Typically, in this method, the alkali metal iodide catalyst to organic halide is used in a molar ratio of about 1:50 to 1:100 (e.g., 1:50).

The reaction temperature used in this method affects reaction kinetics, which in turn affects the purity of the produced compound of formula (I). As temperature decreases, the reaction proceeds more slowly, reducing the amount of impurities. Conversely, as temperature increases, the reaction proceeds more quickly, increasing the amount of impurities. The reaction temperature that can be used to practice this method is in the range of about 0° C. to about 80° C. (e.g., 15° C. or 20° C.-25° C.).

Examples the base described above, include, but are not limited to, amines (e.g., triethylamine and N,N-dimethyl aniline), alkali metal phosphates (e.g., $K_3PO_4$ or $Li_3PO_4$), alkali metal carbonates (e.g., $Na_2CO_3$ or $K_2CO_3$), or a mixture thereof In this method, the molar ratio of the compound of formula (II) to the base can be in the range of about 1:1 to about 1:2 (e.g., 1:1.5).

Completion of the reaction can be monitored by any conventional method, e.g., ultra-violet spectroscopy, infrared spectroscopy, nuclear magnetic resonance, thin layer chromatography, gas chromatography, and high performance liquid chromatography. Upon completion of the reaction, the product can be separated from the reaction mixture by one or more conventional separation methods, such as recrystallization, distillation, chromatography, precipitation, evaporation, or extraction. Suitable extraction solvents include, but are not limited to, ethyl acetate, methyl acetate, methylene chloride, and diethyl ether. The product, thus obtained, may be further purified by the use of one or more conventional purification methods, e.g., chromatography, recrystallization, and precipitation.

Without further elaboration, it is believed that the above description has adequately enabled the present invention. The following examples are, therefore, to be construed as merely illustrative, and not limitative of the remainder of the disclosure in any way whatsoever.

EXAMPLE 1

500 mg of caffeic acid was dissolved in 6 mL of hexamethyl phosphoramide (HMPA). 350 mg exsiccated sodium carbonate ($Na_2CO_3$) was added while stirring. Stirring continued for 30 minutes. At the end of this period a solution of 0.43 mL of phenethyl bromide dissolved in 1 mL HMPA was added slowly to the reaction mixture over a period of 30 minutes. Following the addition, a small amount of potassium iodide was added to the reaction mixture. This mixture was stirred at room temperature for 9 hours after which the temperature was reduced to 15° C. and the reaction mixture was stirred for another 12 hours. Next, the reaction mixture was slowly added to 30 mL of ice water while stirring and extracted with ethyl acetate (3×15 mL). The aqueous layer was acidified by dropwise addition of 1.0 M aqueous HCl and extracted with ethyl acetate. The combined organic extract was washed successively with of 1.0 M HCl (4 mL) and saturated sodium chloride solution (3×15 mL). The organic layer was dried over anhydrous $MgSO_4$, filtered, and concentrated under reduced pressure followed by purification of the crude products by column chromatography, thereby producing caffeic acid phenethyl ester. The yield was 90% and the purity was 99%.

EXAMPLE 2

500 mg of caffeic acid was dissolved in 6 mL of dimethyl sulfoxide (DMSO). 350 mg exsiccated $Na_2CO_3$ was added while stirring. Stirring continued for 30 minutes. At the end of this period a solution of 0.43 mL of phenethyl bromide dissolved in 1 mL DMSO was added slowly to the reaction mixture over a period of 30 minutes. Following the addition, a small amount of potassium iodide was added to the reaction mixture. This mixture was stirred at room temperature for 9 hours after which the temperature was reduced to 15° C. and the reaction mixture was stirred for another 12 hours. Next, the reaction mixture was slowly added to 30 mL of ice water while stirring and extracted with ethyl acetate (3×15 mL). The aqueous layer was acidified by dropwise addition of 1.0 M aqueous HCl and extracted with ethyl acetate. The combined organic extract was washed successively with of 1.0 M HCl (4 mL) and saturated sodium chloride solution (3×15 mL). The organic layer was dried over anhydrous $MgSO_4$, filtered, and concentrated under reduced pressure followed by purification of the crude products by column chromatography, thereby producing caffeic acid phenethyl ester. The yield was 74-79% and the purity was 99%.

EXAMPLE 3

500 mg of caffeic acid was dissolved in 6 mL of a mixture of polyethylene glycol (PEG) and DMSO in which the volume ratio of PEG to DMSO was 1:3. 350 mg exsiccated $Na_2CO_3$ was added while stirring. Stirring continued for 30 minutes. At the end of this period a solution of 0.43 mL of phenethyl bromide dissolved in 1 mL DMSO was added slowly to the reaction mixture over a period of 30 minutes. Following the addition, a small amount of potassium iodide was added to the reaction mixture. This mixture was stirred at room temperature for 9 hours after which the temperature was reduced to 15° C. and the reaction mixture was stirred for another 12 hours. Next, the reaction mixture was slowly added to 30 mL of ice water while stirring and extracted with ethyl acetate (3×15 mL). The aqueous layer was acidified by dropwise addition of 1.0M aqueous HCl and extracted with ethyl acetate. The combined organic extract was washed successively with of 1.0 M HCl (4 mL) and saturated sodium chloride solution (3×15 mL). The organic layer was dried over anhydrous $MgSO_4$, filtered, and concentrated under reduced pressure followed by purification of the crude products by column chromatography, thereby producing caffeic acid phenethyl ester. The yield was 74-79% and the purity was 99%.

OTHER EMBODIMENTS

All of the features disclosed in this specification may be combined in any combination. Each feature disclosed in this specification may be replaced by an alternative feature serving the same, equivalent, or similar purpose. Thus, unless expressly stated otherwise, each feature disclosed is only an example of a generic series of equivalent or similar features.

From the above description, one skilled in the art can easily ascertain the essential characteristics of the present invention, and without departing from the spirit and scope thereof, can make various changes and modifications of the invention to adapt it to various usages and conditions. Thus, other embodiments are also within the claims.

What is claimed is:

1. A method of preparing a compound of formula (I):

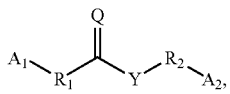
(I)

wherein each of $R_1$ and $R_2$, independently, is $C_{1-8}$ alkylene, $C_{2-8}$ alkenylene, or deleted; each of $A_1$ and $A_2$, independently, is aryl or heteroaryl, optionally substituted with halogen, —CN, —NO$_2$, —OH, —SH, —OR$_3$, —SR$_3$, —R$_3$, —R$_3$OR$_4$, —C(O)R$_3$, —S(O)R$_3$, —S(O)OR$_3$, —NR$_4$R$_5$, —C(O)NR$_4$R$_5$, —OC(O)R$_4$, —NR$_4$C(O)R$_5$; and each of Q and Y, independently, is O, S, or NR$_6$; R$_3$ being $C_{1-4}$ alkyl and each of R$_4$, R$_5$, and R$_6$, independently, being H or $C_{1-4}$ alkyl;

the method comprising:

reacting, in a solvent, a salt of a compound of formula (II):

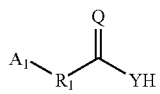
(II)

with an organic halide having the formula X—R$_2$-A$_2$, wherein X is a halogen, in the presence of an iodide catalyst having the formula M-I, wherein M is an alkali metal, to produce the compound of formula (I); and isolating the compound of formula (I) from the solvent.

2. The method of claim 1, wherein each of Q and Y, independently, is O.

3. The method of claim 2, wherein R$_1$ is $C_{2-8}$ alkenylene and R$_2$ is $C_{1-8}$ alkylene.

4. The method of claim 3, wherein R$_1$ is —CH═CH— and R$_2$ is —CH$_2$—CH$_2$—.

5. The method of claim 4, wherein each of A$_1$ and A$_2$, independently, is aryl optionally substituted with —CN, —NO$_2$, —OH, —SH, —OR$_3$, —SR$_3$, —R$_3$, —R$_3$OR$_4$, or —NR$_4$R$_5$.

6. The method of claim 5, wherein each of A$_1$ and A$_2$, independently, is phenyl optionally substituted with —OH or —SH.

7. The method of claim 6, wherein A$_1$ is 3,4-dihydroxyphenyl and A$_2$ is phenyl.

8. The method of claim 1, wherein the iodide catalyst is NaI, KI, LiI, or a combination thereof.

9. The method of claim 8, wherein the iodide catalyst is KI.

10. The method of claim 1, further comprising, before the reacting step, contacting in the solvent the compound of formula (II) with a base to form the salt of the compound of formula (II).

11. The method of claim 10, wherein the base is a phosphate of an alkali metal.

12. The method of claim 1, wherein the solvent is non-genotoxic.

13. The method of claim 12, wherein the solvent is polyethylene glycol, water, dimethyl sulfoxide, acetone, dimethylformamide, or a mixture thereof.

14. The method of claim 13, wherein the solvent is polyethylene glycol.

15. The method of claim 13, wherein the solvent is dimethyl sulfoxide.

16. The method of claim 2, wherein the iodide catalyst is NaI, KI, LiI, or a combination thereof.

17. The method of claim 16, wherein the iodide catalyst is KI.

18. The method of claim 2, further comprising, before the reacting step, contacting in the solvent the compound of formula (II) with a base to form the salt of the compound of formula (II).

19. The method of claim 18, wherein the base is a phosphate of an alkali metal.

20. The method of claim 2, wherein the solvent is polyethylene glycol, water, dimethyl sulfoxide, acetone, dimethylformamide, or a mixture thereof.

21. The method of claim 20, wherein the solvent is polyethylene glycol.

22. The method of claim 20, wherein the solvent is dimethyl sulfoxide.

23. The method of claim 7, wherein the iodide catalyst is NaI, KI, LiI, or a combination thereof.

24. The method of claim 23, wherein the iodide catalyst is KI.

25. The method of claim 7, further comprising, before the reacting step, contacting in the solvent the compound of formula (II) with a base to form the salt of the compound of formula (II).

26. The method of claim 25, wherein the base is a phosphate of an alkali metal.

27. The method of claim 7, wherein the solvent is polyethylene glycol, water, dimethyl sulfoxide, acetone, dimethylformamide, or a mixture thereof.

28. The method of claim 27, wherein the solvent is polyethylene glycol.

29. The method of claim 27, wherein the solvent is dimethyl sulfoxide.

30. The method of claim 1, wherein the reaction is carried out at 15° C.

31. The method of claim 1, wherein the reaction is carried out at 20-25° C.

* * * * *